(12) United States Patent
Greenspan et al.

(10) Patent No.: US 9,198,936 B2
(45) Date of Patent: *Dec. 1, 2015

(54) DEVICES AND METHODS FOR THE REGENERATION OF BONY DEFECTS

(71) Applicant: NovaBone Products, LLC, Alachua, FL (US)

(72) Inventors: David C. Greenspan, Gainesville, FL (US); Srinivas Katta, Gainesville, FL (US)

(73) Assignee: NOVABONE PRODUCTS, LLC, Alachua, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/194,157

(22) Filed: Feb. 28, 2014

(65) Prior Publication Data

US 2014/0178453 A1 Jun. 26, 2014

Related U.S. Application Data

(63) Continuation of application No. 13/039,627, filed on Mar. 3, 2011, now Pat. No. 8,795,702.

(60) Provisional application No. 61/310,129, filed on Mar. 3, 2010.

(51) Int. Cl.
| | | |
|---|---|---|
| *A61K 33/42* | (2006.01) | |
| *A61K 38/39* | (2006.01) | |
| *A61K 45/06* | (2006.01) | |
| *A61L 27/24* | (2006.01) | |
| *A61L 27/36* | (2006.01) | |
| *A61L 27/46* | (2006.01) | |
| *A61L 27/56* | (2006.01) | |

(52) U.S. Cl.
CPC .............. *A61K 33/42* (2013.01); *A61K 38/39* (2013.01); *A61K 45/06* (2013.01); *A61L 27/24* (2013.01); *A61L 27/365* (2013.01); *A61L 27/3633* (2013.01); *A61L 27/46* (2013.01); *A61L 27/56* (2013.01); *A61L 2430/02* (2013.01)

(58) Field of Classification Search
CPC ....... A61K 33/42; A61K 38/39; A61K 45/06; A61L 2430/02; A61L 27/24; A61L 27/3633; A61L 27/365; A61L 27/46; A61L 27/56
See application file for complete search history.

(56) References Cited

U.S. PATENT DOCUMENTS

| | | |
|---|---|---|
| 4,851,046 A | 7/1989 | Low et al. |
| 5,320,844 A | 6/1994 | Liu |
| 5,912,225 A | 6/1999 | Mao et al. |
| 5,977,204 A | 11/1999 | Boyan et al. |
| 6,027,742 A | 2/2000 | Lee et al. |
| 6,045,555 A | 4/2000 | Smith et al. |
| 6,153,212 A | 11/2000 | Mao et al. |
| 6,166,173 A | 12/2000 | Mao et al. |
| 6,187,047 B1 | 2/2001 | Kwan et al. |
| 6,224,913 B1 | 5/2001 | Ducheyne et al. |
| 6,238,687 B1 | 5/2001 | Mao et al. |
| 6,322,797 B1 | 11/2001 | Mao et al. |
| 6,328,990 B1 | 12/2001 | Ducheyne et al. |
| 6,344,496 B1 | 2/2002 | Niederauer et al. |
| 6,395,036 B1 | 5/2002 | Czernuszka et al. |
| 6,413,538 B1 | 7/2002 | Garcia et al. |
| 6,417,166 B2 | 7/2002 | Liu |
| 6,569,466 B2 | 5/2003 | Ducheyne et al. |
| 6,764,517 B2 | 7/2004 | Yamamoto et al. |
| 6,902,584 B2 | 6/2005 | Kwan et al. |
| 6,949,251 B2 | 9/2005 | Dalai et al. |
| 6,969,501 B2 | 11/2005 | Sapieszko et al. |
| 6,991,802 B1 | 1/2006 | Ahola et al. |
| 6,991,803 B2 | 1/2006 | Sapieszko et al. |
| 7,014,640 B2 | 3/2006 | Kemppainen et al. |
| 7,156,880 B2 | 1/2007 | Evans et al. |
| 7,166,133 B2 | 1/2007 | Evans et al. |
| 7,189,263 B2 | 3/2007 | Erbe et al. |
| 7,229,971 B2 | 6/2007 | Tanaka et al. |
| 7,241,459 B2 | 7/2007 | Fechner et al. |
| 7,531,004 B2 | 5/2009 | Bagga et al. |
| 7,534,451 B2 | 5/2009 | Erbe et al. |
| 7,544,212 B2 | 6/2009 | Li et al. |
| 7,544,496 B2 | 6/2009 | Gower et al. |
| 7,547,499 B2 | 6/2009 | Veregin et al. |

(Continued)

FOREIGN PATENT DOCUMENTS

| | | |
|---|---|---|
| WO | WO98/46164 | 10/1998 |
| WO | WO2013/188336 A2 | 12/2013 |

OTHER PUBLICATIONS

European Search Report received in Application No. 11751335.8 dated Jul. 7, 2014.

(Continued)

*Primary Examiner* — Abigail Fisher

(74) *Attorney, Agent, or Firm* — Brinks Gilson & Lione

(57) ABSTRACT

This invention relates to methods for producing a composite bone graft material that can regenerate bony defects in the body. The invention further relates to methods that allow for the production of bioactive glass particles used in the composite that have been surface treated to allow for the production of a highly porous composite that can hold significant amounts of body fluid or other molecules that will aid in the regenerative process. The method of surface treatment allows for the manufacture of a suitable implantable composite while retaining the unique osteostimulative properties that are associated with bioactive glass particles.

17 Claims, No Drawings

(56) References Cited

U.S. PATENT DOCUMENTS

| | | |
|---|---|---|
| 7,578,845 B2 | 8/2009 | Nies et al. |
| 7,621,963 B2 | 11/2009 | Simon et al. |
| 8,252,055 B2 | 8/2012 | McKay |
| 8,795,702 B2 * | 8/2014 | Greenspan et al. ........... 424/422 |
| 2002/0055143 A1 | 5/2002 | Bell et al. |
| 2002/0112981 A1 | 8/2002 | Cooper et al. |
| 2005/0251267 A1 | 11/2005 | Winterbottom |
| 2007/0162151 A1 * | 7/2007 | Chang et al. ............... 623/23.56 |
| 2008/0187571 A1 | 8/2008 | Clineff et al. |
| 2010/0312355 A1 | 12/2010 | Yahav et al. |
| 2011/0217388 A1 | 9/2011 | Greenspan et al. |
| 2013/0331898 A1 | 12/2013 | Nyemscek et al. |
| 2014/0017281 A1 | 1/2014 | Pomrink et al. |

OTHER PUBLICATIONS

International Search Report completed Apr. 14, 2011 in International Application No. PCT/US2011/026961, filed Mar. 3, 2011.

English language translation of the International Preliminary Report on Patentability dated Sep. 4, 2012, from corresponding International Application No. PCT/US2011/026961, filed Mar. 3, 2011.

International Search Report and Written Opinion received in PCT Application No. PCT/US14/70633 dated Mar. 25, 2015.

* cited by examiner

DEVICES AND METHODS FOR THE REGENERATION OF BONY DEFECTS

This application is a continuation application of U.S. patent application Ser. No. 13/039,627, filed Mar. 3, 2011, which claims the benefit of U.S. Provisional Application No. 60/310,129, filed Mar. 3, 2010, the entire contents of which are hereby incorporated herein by reference.

BACKGROUND

There are dozens of materials used today for the repair and regeneration of bony defects. Bone is composite material that is comprised of collagen, cells, a form of calcium hydroxyapatite crystals and small quantities of other proteins and organic molecules. The chemistry and physical nature of this composite affords it unique properties of high strength, rigidity, and an ability to adapt to changing loads in the body. However, when injuries to bone occur it is sometimes necessary to find a way to fill voids or gaps, and to encourage the repair and regeneration of the bone tissue.

Autograft bone, usually taken from the iliac crest remains the gold standard for filling bony defects. Autograft bone is said to be osteoinductive; that is it will grow bone wherever it is placed in the body due to the cellular content and the presence of growth factors. Despite the generally favorable results from autograft transplants, there remain serious concerns about donor site morbidity, graft collapse and length of hospital stay in comparison to using other materials. Allograft bone in various forms has also been used extensively as bone grafts with mixed results. Allograft, while yielding outcomes generally similar to autograft, is expensive to produce, is generally slower to incorporate, is variable in performance due to different processing methods and carries the potential risk of infection and disease transmission, though that risk is quite small.

Due to the issues with autograft and allograft bone, a number of other materials, including xenograft and synthetic biomaterials have been used in various bone grafting procedures. Hydroxyapatite bone substitutes have been used somewhat successfully in certain long bone fractures. These materials are said to be osteoconductive. That is, they allow bone to grow along the surface of the material and actually act as a scaffold for new bone growth. This osteoconductive ability depends on the composition, physical structure, porosity and method of manufacture of these materials.

Hydroxyapatite materials have been used mainly in dental procedures and in some long bone grafting procedures. In cervical fusion procedures there have been few reports of the use of synthetic hydroxyapatite. In a clinical study by Zdeblick, coralline-derived HA (ProOsteon, Interpore Cross, Irvine, Calif.) was evaluated in non-instrumented cervical fusion with less than half the grafts incorporating. In that study 14% of grafts extruded and 29% collapsed. Tri calcium phosphates are another form a ceramic material that is used, usually in a porous form for non-load bearing bone grafts. While the success has been good in small defects, the particulate material is somewhat difficult to work with and cannot always be maintained in the surgical site.

Calcium sulfate materials are a form of highly resorbable ceramic bone graft substitute. These have been used with some success as well, but are again limited in their use due to the particulate nature of the material and the difficulty of keeping it in the surgical site. In addition, there have been reports that the material resorbs too quickly, leaving bone voids and poor clinical outcomes. In addition to the synthetic bioceramic materials, there has been some attempt to use xenograft bone for repair and regeneration. However, there is always a risk of antigenicity from this bone, derived mainly from the atelo groups on the collagen fibers within the bone structure. There is also a fear of transmission of CJD (Crutzfeld Jacobs Disease) from the bovine source, although the risk is actually quite small. However, these elements have severely limited its use.

Calcium, sodium phosphosilicate materials, commonly referred to as bioactive glasses are another class of bioceramic material that has been successfully used in bone graft procedures. Calcium sodium phosphosilicates are unique in that they are not only osteoconductive but are also osteostimulative. When exposed to an aqueous environment, such as found in bony defects, the material releases specific ions (Ca, P, Si, Na) in certain concentrations over time. Due to this release of ions, the surface changes and becomes an excellent structure to support cell adhesion, proliferation and differentiation.

Numerous in-vitro and in-vivo studies have shown that these compounds stimulate the rapid proliferation and differentiation of osteoblasts compared with other bone graft materials. In-vitro studies have demonstrated that exposure of osteoblasts to bioactive glass actually upregulates a family of genes that are involved in cellular proliferation as well as differentiation into an osteoblasts phenotype. Additional studies have demonstrated that the ionic extracts released from the bioactive glass particles can actually upregulate primary osteoblasts compared with control samples, accelerating the rate of cell differentiation. Earlier cell culture studies with primary osteoblasts had shown that after 21 days, three-dimensional bone nodules greater than 3 mm in length had formed when cultured on bioactive glass disks. Recent studies have also demonstrated that certain concentrations of the extracts released from bioactive glasses have a pro-angiogenic response. This property would be especially important in the early stages of wound healing and creating an environment favorable for new bone formation. In light of the results with the ionic extracts described and the surface reactive nature of the bioactive glass when exposed to an aqueous environment, those results are consistent with our knowledge of these materials and help to explain the robust bone regenerative properties of this material.

Recently, a clinical study was published comparing bioactive glass (NovaBone, NovaBone Products, LLC) with autograft in adolescent idiopathic scoliosis cases. The average follow-up was 40 months. The results showed a higher complication rate with autograft compared with the bioactive glass (not statistically significant) and a greater loss of correction with autograft compared with the bioactive glass ($p=0.025$) which was statistically significant. In addition, blood loss was significantly less in the bioactive glass group (1280 mL in the autograft group versus 853 mL in the bioactive glass group). The authors concluded that bioactive glass was effective as a bone graft in these procedures and performed equivalently with autograft. However, in the particulate form, bioactive glass particles are limited by the same constraints as the other bioceramic materials.

In an attempt to improve on the use of particulate materials, there have been a number of composite and putty-like materials that have been developed for bone regeneration. Because calcium phosphate materials are very similar to bone mineral these have been incorporated with many other bioresorbable and non-resorbable polymers. One of the most often cited and used materials in this regard is collagen, because the combination of the calcium phosphate and collagen is close in composition to natural bone. In one example a solid composite is formed by taking collagen from about 5% up to 75% and precipitating a calcium salt and a phosphate containing salt to form a homogeneous composite (U.S. Pat. No. 5,320,844). While this produces a workable material, it is limited by the size and shape because the precipitation of the soluble calcium and phosphate materials will preferentially occur on the surface and the composition of the composite will vary throughout the structure. This would naturally lead to variable properties of the material. Another variation of this precipitation process is disclosed in U.S. Pat. No. 6,395,036 wherein a matrix of a bioresorbable polymer (collagen) is exposed to different solutions of calcium ions and phosphate ions such that there is more hydroxyapatite in the body of the composite than on the surface. This is achieved through careful control of pH and concentration of the ionic solutions as well as the order and rate at which they are exposed to the collagen matrix.

In another example (U.S. Pat. No. 6,187,047) dilute solutions of collagen, type I, are mixed with fine particles of calcium phosphate, said particles being 5 microns or less. This process forms a porous 3-dimensional matrix that maintains its structural integrity for at least 3 days and maintains porosity for up to 14 days. While this method allows for the immobilization of the particles initially, once the material starts to degrade, the release of small particles can be problematic is it is know that small particles can cause an osteolytic process that results in inflammation and bone resorption.

U.S. Pat. No. 6,417,166 discloses a thin flexible mineralized collagen membrane for such uses as guided barrier membranes and periodontal defect repair as well as bone grafts and wound repair. The process utilizes up to 70% collagen with 30% to 70% calcium phosphate minerals. The process relies on the addition of calcium solutions and phosphate solutions to a collagen slurry and casting the slurry into a mold and drying said mixture. This is said to form a mineralized collagen composite. This process is severely limited, however, to thin small membranes as the process is ineffective and very expensive for making larger shapes and forms.

Other examples of collagen-calcium phosphate composites can be found in U.S. Pat. No. 6,764,517 and U.S. Pat. No. 6,902,584. In these patents, a 3-dimensional mineralized collagen composite is produced by creating collagen slurry, freezing and lyophilizing the mixture and then subjecting it to calcium and phosphate solutions to form a porous mineralized matrix. These patents further describe adding a soluble collagen in an additional step and lyophilizing that mixture to form the porous composite. The inventions further describe the ability to use various cross-linking agents to enhance physical stability and increased implant resonance time and shape retention. While this technology can produce an improvement over the previous technologies, the manufacturing process consists of many different steps which become costly and very time consuming.

Further refinements of these general methods for producing collagen—calcium phosphate composite materials can be found in U.S. Pat. No. 7,156,880 and U.S. Pat. No. 7,166,133. These inventions describe the manufacture of implants that consist of an osteoconductive matrix that comprises a blend of both insoluble and soluble collagen where at least a portion of the implant is porous. In addition these structures may contain osteoinductive molecules as well as biodegradable synthetic polymers. The inventions also describe the incorporation of ceramic materials such as calcium phosphate, calcium sulfate or hydroxyapatite in the form of discrete particles, rather than forming the compounds through precipitation of salts.

More recent technologies such as those found in U.S. Pat. No. 7,531,004 and U.S. Pat. No. 7,534,451 describe a bone restorative composite material that consists of a resorbable polymer that can be collagen, a range of meso, micro and macro porosity to allow for the inclusion of fluid and to assist in bone ingrowth, as well as the inclusion of calcium phosphate particles. The inventions further utilize a specific oxidation-reduction reaction of very specific calcium and phosphorous containing salts to precipitate calcium phosphate within the collagen structure. These devices typically require very precise control of the chemistry in order to obtain the desired results of the precipitation of the calcium phosphate materials and appear to be limited to calcium based osteoconductive materials.

While the above referenced composite materials are an improvement over the use of particulate materials there is still a need for a cost-effective material that can be widely used in bone regenerative surgery, and that will enhance the bone healing. While calcium phosphate materials are osteoconductive the osteostimulative effects of calcium-sodium phosphosilicate materials such as described above would enhance the robustness of bone healing. Such materials could also carry additional bio-molecules, growth factors or other therapeutic agents. Therefore, it is an object of this invention to provide a cost effective, easily manufactured bone restorative material that enhances the bone regeneration of damaged osseous tissue, will remain in the surgical site, and gradually resorb over time to leave only natural bone tissue in the regenerated site.

SUMMARY OF THE INVENTION

The present invention is directed to a bone regenerative implantable composition and methods for repairing or regenerating bony defects comprising implanting a bone regenerable composition. In some embodiments, the bone regenerative implantable composition comprises from about 2% to about 20% by weight of a bioresorbable polymer and from about 10% up to about 98% bioactive material particles that have been pre-reacted with a buffer. In another embodiment, the bioactive material is pretreated with a buffer for about 1 hour to 24 hours. In further embodiments, the buffer is TRIS buffer. In certain embodiments, the bioresorbable polymer is collagen. In further aspects, the composition further comprises an extracellular matrix molecule selected from the group consisting of integrins, fibronectin, vitronectin, osteopontin, bone sialoprotein thrombospondin, and fibrinogen, or a homo or copolymer of glycolides, acrylates, lactic acids, and caprolactone.

In certain aspects, the bioactive material is calcium sodium phosphosilicate (bioactive glass). In further aspects, the bioactive material is a calcium phosphate having the general chemical formula $Ca_5(PO_4)_3X$, wherein X is OH (hydroxyapatite), F (fluorapatite), or Cl (chlorapatite). In one aspect, the bone regenerable composition is implanted in a subject in need thereof.

DETAILED DESCRIPTION

The present application related compositions and methods suitable for bone regeneration. In some aspects, the compositions and methods relate to porous composite structures with enhanced bone regeneration capabilities, and which remain in the surgical site, adsorb body fluids, blood, bone marrow aspirate and hold other biomolecules. In certain embodiments, the porous composite structure is a bioactive material. Bioactive materials suitable for the present invention are any surface active materials able to chemically bond to body tissue. Examples of bioactive materials suitable for the compositions and methods include bioactive glasses, glass ceramics and ceramics. Bioactive glasses are typically amorphous whereas bioactive glass ceramics typically contain crystalline particles embedded in an amorphous glass phase. Bioactive ceramics typically have a crystalline structure. Thus, the bioactive materials suitable for the present invention may be amorphous, crystalline or combinations thereof (i.e., amorphous particles having some crystalline domains, crystalline particles having some amorphous domains or mixtures of crystalline and amorphous particles).

A bioactive material suitable for the present compositions and methods may be prepared from calcium sodium phosphosilicate particles or calcium phosphate particles, or combinations thereof. In some embodiments, sodium phosphosilicate particles and calcium phosphate particles may be present in the compositions in an amount of about 1% to about 99%, based on the weight of sodium phosphosilicate particles and calcium phosphate particles. In further embodiments, calcium phosphate may be present in the composition in about 1%, about 2%, about 3%, about 4%, about 5%, about 6%, about 7%, about 8%, about 9%, or about 10%. In certain embodiments, calcium phosphate mat be present in the composition in about 5 to about 10%, about 10 to about 15%, about 15 to about 20%, about 20 to about 25%, about 25 to about 30%, about 30 to about 35%, about 35 to about 40%, about 40 to about 45%, about 45 to about 50%, about 50 to about 55%, about 55 to about 60%, about 60 to about 65%, about 65 to about 70%, about 70 to about 75%, about 75 to about 80%, about 80 to about 85%, about 85 to about 90%, about 90 to about 95%, or about 95 to about 99%. Some embodiments may contain substantially one of sodium phosphosilicate particles and calcium phosphate particles and only traces of the other. The term "about" as it relates to the amount of calcium phosphate present in the composition means±0.5%. Thus, about 5% means 5±0.5%.

In certain embodiments, the particles may have particular size and/or geometry. For example, the particles may be spherical (e.g., microspheres) or may possess any other geometry such as flat surfaces (e.g., microdisks). In some embodiments, the particle size may be about 50 microns to about 5 mm in diameter. In some embodiments, the average particle size is about 500 to about 1500 microns, about 1000 to about 2000 microns or from about 1200 micron to about 2500 microns. In certain embodiments, the particles may have average diameter of about 50, about 100, about 200, about 500, about 750, about 1000, about 1200, about 1400, about 1600, about 1800, about 2000, about 2200, about 2500, about 2750, about 3000, about 3500, about 4000, about 4500, or about 5000 microns. As used in this paragraph, the term "about" means±100 microns or ±10% of the average particle size, whichever is smaller. Thus, about 50 microns means 50±5 microns whereas about 3500 microns means 3500±100 microns.

The bioactive material may be a bioactive glass or glass ceramic. The bioactive material may be calcium phosphate or calcium sodium phosphosilicate particles. The bioactive material may be prepared by any suitable technique known to those skilled in the art. For example, the particles may be native calcium phosphate or sodium phosphosilicate particles (amorphous bioactive glass particles). The calcium phosphate materials may be naturally occurring or synthetic. The calcium phosphate may be amorphous or crystalline or combinations thereof. Illustrative calcium phosphates have the general chemical formula $Ca_5(PO_4)_3X$, where X is OH (hydroxyapatite), F (fluorapatite), or Cl (chlorapatite). Such materials are also known as "apatites." The term "hydroxyapatite" or "HA" as used herein, generally refers to a form of apatite with the formula $Ca_5(PO_4)_3(OH)$. More typically, HA is represented as $Ca_{10}(PO_4)_6(OH)_2$ to denote that the crystal unit cell comprises two molecules. Hydroxylapatite is the hydroxylated member of the complex apatite group. The hardness of hydroxyapatite may be altered by replacing the OH ion with other anions (e.g., fluoride, chloride or carbonate). Additionally, HA has a relatively high affinity for peptides, making it an ideal carrier for the delivery and sustained release of polypeptides over long periods of time in situ.

The bioactive glass of the present invention may comprise approximately equal molar ratios of CaO and $SiO_2$ as main components such that it has substantially the same composition as that of the β-wollastonite. The bioactive glass may be crystallized as a needle-like structure and sintered to increase its mechanical strength. The bioactive glass may further comprise $P_2O_5$ to improve biocompatibility.

Bioactive glass that may also be suitable include glasses having about 40 to about 60 wt-% $SiO_2$, about 10 to about 34 wt-% $Na_2O$, up to about 20 wt-% $K_2O$, up to about 5 wt-% MgO, about 10 to about 35 wt-% CaO, up to about 20 wt-% $B_2O_3$, about 0.5 to about 12 wt-% $P_2O_5$. The bioactive glass may additionally contain up to 10-wt % $CaF_2$. In a certain embodiment, the bioactive glass has the following composition 53 wt-% $SiO_2$, 6 wt-% $Na_2O$, 12 wt-% $K_2O$, 5 wt-% MgO, 20 wt-% CaO, and 4 wt-% $P_2O_5$.

In some embodiments, the particles are sintered to form porous particulate made from the bioactive glass particles. In one embodiment, fine particles of the bioactive glass are mixed with a sacrificial polymer and a binder to create a pre-shaped construct (e.g., a block or disk). The construct is then heated under specific conditions that allow a welding of the particles together without completely melting them. This process uses a temperature high enough to allow for the polymer material to burn off leaving a porous structure. The compression strength as well as the porosity of the construct may be controlled by varying the type and the amount of the sacrificial polymer and the sintering time and temperature used. Porosities as high as 90% may be achieved under suitable conditions. The pores in the bioactive glass material range from about 10 microns to about 5100 microns with an average pore size of 100±50 microns, 200±50 microns, 300±50 microns, 400±50 microns, 500±50 microns, 600±50 microns or 700±50 microns.

The bioactive glass material may be ground with mortar and pestle prior to converting it to a paste. Any other method suitable for grounding the bioactive glass material may be used. In one embodiment, the ground bioactive glass material may be mixed with other constituents to produce templates or granules that may be formed into a paste that can be shaped before further treatments are made. For example, a suitable bioresorbable polymer may be used to prepare a paste of a bioactive material (for example, glass or ceramic material). In one embodiment, a paste of a non-crystalline, porous bioactive glass or ceramic material is prepared that permit in vitro formation of bone tissue when exposed to a tissue culture medium and inoculated with cells.

It is surprisingly been found that when the paste of a pre-treated bioactive glass or ceramic particles and a bioresorbable polymer is freeze-dried, it retains the osteostimulative effect of the glass while retaining its physical integrity and remaining wettable. Thus, in one embodiment, the bioactive glass or ceramic particles are treated with certain buffer solutions prior to the preparation of the paste. The pre-treatment prepares the surface of the particles for cell adhesion and controls pH prior to the exposure of the particles with cells. In this context, the bioactivity and bone formation using the glass particles of the present invention may be enhanced by treating the glass particles with a buffer solution prior to mixing the particles with a bioresorbable polymer.

In certain embodiments, the pre-treatment buffer solution has a starting pH of from about 6 to about 8 but may reach an end pH of about 9.5. Examples of buffers that might be suitable for the pre-treatment of the present invention include mixed sodium phosphate salts (such as Sørensen's Phosphate buffer, Millonig's Phosphate buffer, Karlsson and Shultz Phosphate buffer, Maunsbach Phosphate buffer, and Phosphate Buffered Saline (PBS); buffer pH of about 6.4-8.0), TAPS (3-{[tris(hydroxymethyl)methyl]amino}propanesulfonic acid; buffer pH of about 7.7-9.1), Bicine (N,N-bis(2-hydroxyethyl)glycine; buffer pH of 7.6-9.0), Tricine (N-tris(hydroxymethyl)methylglycine; buffer pH about 7.4-8.8), Tris (tris(hydroxymethyl)methylamine; buffer pH of about 7.5-9.0), HEPES (4-2-hydroxyethyl-1-piperazineethanesulfonic acid; buffer pH of about 6.8-8.2), TES (2-{[tris(hydroxymethyl)methyl]amino}ethanesulfonic acid; buffer pH of about 6.8-8.2), MOPS (3-(N-morpholino)propanesulfonic acid; buffer pH of about 6.5-7.9), PIPES (piperazine-N,N'-bis(2-ethanesulfonic acid); buffer pH of about 6.1-7.5), Cacodylate (dimethylarsinic acid; buffer pH of about 5.0-7.5), SSC (saline sodium citrate; buffer pH of about 6.5-7.5), or MES (2-(N-morpholino)ethanesulfonic acid; buffer pH of about 5.5-6.7). Any other buffer having appropriate pH buffering range of about 6 to about 8 might be suitable.

In certain embodiments, the end pH does not exceed 9.5, 9.4, 9.3, 9.2, 9.1, 9.0, 8.8, 8.9, 8.7, 8.6, 8.5, 8.3, 8.2, 8.1, or 8.0.

Depending on the buffer used, the bioactive glass or ceramic particles may be pretreated for different periods such that the particles become suitable for preparing constructs suitable for bone regeneration. Pre-treating the bioactive glass or ceramic particles much longer than necessary to activate them may deactivate the particles. Similarly, if the bioactive glass or ceramic particles are not pre-treated long enough, they may remain too active and attempts to convert them into a paste may encounter premature gellation of the paste. In some embodiments, the bioactive glass or ceramic particles may be pretreated with the buffer for as short as 30 minutes. Other embodiments of the bioactive glass may require pretreatment as long as 24 hours. In some embodiments, the bioactive glass may be pretreated about 1 to about 2 hours, about 3 to about 4 hours, about 5 to about 6 hours, about 7 to about 8 hours, about 9 to about 10 hours, about 11 to about 12 hours, about 13 to about 14 hours, about 15 to about 16 hours, about 17 to about 18 hours, about 19 to about 20 hours, about 21 to about 22 hours, or about 23 to about 24 hours. Some bioactive glasses may require pretreatments longer than 24 hours. As used here in the context of pre-treatment time, the term "about" means±30 minutes. A person skilled in the art can easily design simple experimental procedures to determine the optimum pretreatment time for any given buffer and bioactive glass or ceramic particles.

A paste of the pre-treated bioactive glass or ceramic particles and a bioresorbable polymer may be prepared using methods known to those skilled in the art. The paste may then be shaped into a desirable form and freeze dried before contacting the freeze-dried paste with a culture medium or implanted into an animal.

Thus, one embodiment of the present invention relates to methods of forming bone tissue comprising providing porous bioactive material, immersing the porous bioactive material in a buffer solution, isolating the pre-treated particles, forming a paste of the pre-treated particles and a bioresorbable polymer, shaping the paste to a construct with the desired shape, and freeze-drying the construct. The freeze-dried construct so obtained may be immersed in a tissue culture medium to produce a construct having enhanced bone cell activity when cells are inoculated on its surface. In certain embodiments, the construct is inoculated with cells and bone tissue is permitted to form thereon.

The properties of the construct, i.e. porosity, pore size and compressive strength, can be adjusted to a desired level by adjusting the amount and type of the bioresorbable polymer used to prepare the paste, the choice of the particle size, the buffer used to pre-treat the particles, and length of time the particles are exposed to the pre-treatment solution.

In certain embodiments, the lyophilized construct may be subjected to crosslinking or a fixation treatment to preserve the structural integrity of the construct. Any reagent suitable for fixation/crosslinking of biological constructs may be suitable. Such fixation/crosslinking may include exposing the freeze-dried construct to gluteraldehyde and may occur without any mechanical, hydrostatic, or other external stress placed on the construct. Fixing the construct without application of external stress would allow for some shrinkage of the construct to occur without affecting the orientation of the bioresorbable polymer or the biomechanical properties of the construct.

In certain embodiments, the construct is inoculated with cells and bone tissue is permitted to form thereon. In further embodiments, the construct is inoculated with cells from the patient by implanting the construct in a patient. In certain embodiments, the construct is inoculated with osteoblasts or precursor cells to osteoblasts. The osteoblasts or the precursor to the osteoblasts may have been extracted from the patient that is to receive the construct as an implant. In certain embodiments, the osteoblasts or its precursor may be extracted from a donor. In further embodiments, the porous bioactive glass constructs may be implanted in sites where there is an immediate need for bone.

In some embodiment, the bioresorbable polymer suitable for the present invention is any biological polymer that facilitates cell adhesion. Thus, in some embodiments, the freeze-dried construct may be treated with integrins or other extracellular matrix molecules, such as various forms of collagens, fibronectin, vitronectin, osteopontin, bone sialoprotein thrombospondin, and fibrinogen. Other suitable bioresorbable polymers may include homo and copolymers of glycolides, acrylates, lactic acids, and caprolactone. Additional bioresorbable polymers suitable for the present invention are those described in U.S. Pat. Nos. 6,322,797, 6,238,687, 6,166,173, 6,153,212, and 5,912,225, each of which is hereby incorporated by reference. In some embodiments, the construct may further comprise a polysaccharide (such as dextran, dextran sulfate, diethylaminoethyl dextran, or dextran phosphate or mixtures thereof).

In some embodiments, Type I collagen may be used as the bioresorbable polymer. Type I collagen is the most plentiful in the body and has been widely used for medical applications. It can be derived from bovine, ovine or other sources. In some embodiments, collagen is extracted from the native source, for example, bovine hides using a neutral or dilute acidic buffer. In this extraction process, a slurry of collagen in an aqueous buffer, either acidic around pH 3 or by a slightly different process a neutral pH around 7, is produced. In another form of production, the acid treated collagen is further broken down enzymatically to remove the telo peptides at the end of the collagen chains. This treatment renders the collagen more soluble and may lessen any possible antigenicity caused by the telo groups on the ends of the collagen fibrils. The concentration of the collagen varies anywhere from 3 mg/mL of solution to upwards of 50 mg/mL. The samples were evaluated for wickability and retention of fluids after wetting. To achieve this, the samples (in triplicate) were cut into 1 inch×1 inch sizes. Liquids such as water, saline or sheep blood were used in 1:1 volumetric ratio dependent on the sample size. Liquids were added in increments (drops) to the strip and the wicking property was evaluated dependent on the absorption time of the liquids and the volume of fluids required to completely saturate the samples.

Wicking Evaluation Parameters:
Sample absorption ratio—with a desired volume ratio of 1:1 or more;
Absorption time—the shorter the better with 1-2 seconds deemed acceptable;
After wetting, the samples that did not require any manipulation for complete saturation were deemed desirable;
Samples that wet thoroughly through all surfaces were deemed desirable;

After wetting, the samples were evaluated for shrinkage, homogeneity, fluid retention and structural integrity. After wetting the samples were measured to verify the size and calculate the shrinkage if any. Shrinkage of 5-10-% upon wetting was considered acceptable.

After wetting, the samples were visually inspected for homogeneity making sure the particles were uniformly distributed in the composite samples. A 100 g calibration standard weight was placed on the wetted samples to evaluate the fluid retention property.

Fluid Retention Evaluation Parameters:
After wetting, a 100 g calibrated weight standard was placed on the samples;
The samples were typically able support the weight of the standard without collapsing;
With a 100 gm load, desirable samples typically retained 90%-100% of the fluid. Samples were evaluated visually and fluid retention capability of the samples were evaluated by counting the drops of fluid expressed out after weight placement;

The samples were manipulated to evaluate the structural integrity. Upon manipulation desirable samples exhibit some level of shape/memory retention quality. Desirable samples retain a level of moisture, maintaining consistency without disintegrating.

In the initial experiments, it was found that the reactivity (ionic release) of the bioactive glass particles caused a reaction with the collagen used that prevented an adequate working time to allow for the shaping and subsequent processing of the implants. This resulted in a material ratio that would not absorb liquid and resulted in poor handling characteristics. Ability to absorb liquid is important in the performance of the implanted material.

Experiment 1

Three type I collagens were used in the following experiments: (a) acid swollen gel ("ASG") pH 3, (b) digested, pepsin treated collagen (higher solubility) ("DM3"), or (c) base treated gel, pH 7, all at 10 mg/mL concentration. To the collagen slurry, suspension, solution, or gel, is was added 90% bioactive glass, porous particles, 1 mm-2 mm size range. The particles were mixed with the collagen slurry using a low speed mixer and the resultant mixture was poured into a mold. It was noted that during mixing the viscosity of the solution began increasing prior to pouring the mixture, indicating that ions released from the particles, specifically Na, Ca or Si were interacting with the active side chains of the collagen causing something of a cross-linking of the chains. After getting the slurry into the molds, the mixture was lyophilized (i.e., frozen and then subjected to a vacuum in order to sublime the frozen water). This process resulted in a dry collagen-particulate matrix. Upon placing drops of water on the surface of the material it was noted that there was no adsorption of the liquid, indicating that the reaction of the particles with the collagen in the mixing vessel had rendered the material relatively inactive.

Experiment 2

In these experiments, the acid swollen gel ASG was mixed with the pepsin treated collagen DM3 at 1:2, 1:1 and 2:1 ratios. The total collagen concentration used was 10 mg/mL along with a 97% by weight concentration of particles. The particles were mixed with the collagen slurry and it was noticed that the slurry began to gel prior to pouring into the molds, just as in the previous experiment. After the lyophilization process was complete, the resulting materials were wetted and again it was noted that liquid was not absorbed into the material. It was also noted that particles of the bioactive glass were falling out of the composite material upon handling.

Experiment 3

In this experiment, the particle size of the bioactive glass was reduced to 800 microns to 1.7 mm and a combination of ASG/DM3 collagen at a 2:1 ratio was used. The loading of the particulates was lowered from 97% to 95%. The outcome was similar to that in Experiment 2 in that the mixture was noted to react in the mixer and the slurry began to gel, limiting the working time of the mixtures. In addition, while this ratio of the ASG to DM3 collagen allowed for some adsorption of liquid when tested after the lyophilization process, the handling characteristic resulted in a material that did not hold together after wetting.

From the above experiments it appears that using particles of bioactive glass in the native state results in material that is too reactive to allow for the proper open pore structure of the collagen-particulate composite, and changes the surface so that it is not possible to adsorb the fluids that are so important to the proper functioning of the device. Therefore, one embodiment of the present invention is to pre-react the particles in such a manner that the surface ionic reactivity would be reduced enough so that the particles did not interfere with the proper setting of the collagen structure while maintaining enough reactivity so that the composite material exhibited the unique osteostimulative properties imparted by the bioactive glass particles. Therefore, one pre-reaction matrix was set up in order to reduce the surface ionic activity enough to allow proper formation of the composite materials. The process of pre-reacting the particulate depends on the particle size, volume of particles used and the reagent used. Because the reactivity is sensitive to the surface area of particles exposed to the solution and to the volume of the solution, it will be appreciated that the examples below are only for the specific volumes and mass of particles used. The process consists of reacting a specific weight of particulate, in this case 25 g of particles with a surface area of 1 $m^2/g$ in 200 ml of a tris hydroxyl-aminomethane (TRIS) buffer that is titrated to a pH of 7.2 using hydrochloric acid. Particles were reacted for 1, 2, 6, 12 and 18 hrs and the starting and ending pH measured. The rise in pH is related to the amount of ions released from the particles.

| Date | Sample | Start pH | End pH | Particle Size |
|------|--------|----------|--------|---------------|
| 8/25 | P1 hr | 7.32 | 8.08 | 1-2 mm |
| 8/25 | P18 hr | 7.31 | 8.73 | 1-2 mm |
| 8/25 | BG1p | 7.34 | 8.75 | 1-2 mm |
| 8/25 | BG18p | 7.32 | 9.35 | 1-2 mm |
| 9/21 | P6p | 7.21 | 8.77 | 1-2 mm |
| 9/21 | P6p | 7.21 | 8.77 | 1-2 mm |
| 9/22 | P12p | 7.25 | 9.15 | 1-2 mm |
| 9/22 | P18p | 7.21 | 9.24 | 1-2 mm |
| 9/23 | P6p #1 | 7.21 | 8.89 | .8-1.4 mm |
| 9/23 | P6p #2 | 7.21 | 8.98 | .8-1.4 mm |
| 10/14 | P18p #1 | 7.33 | 9.42 | .8-1.4 mm |
| 10/14 | P18p #2 | 7.33 | 9.49 | .8-1.4 mm |
| 10/14 | P18p #3 | 7.33 | 9.36 | .8-1.4 mm |
| 10/14 | P18p #4 | 7.33 | 9.42 | .8-1.4 mm |
| 10/14 | P18p #5 | 7.33 | 9.22 | .8-1.4 mm |
| 10/14 | P18p #6 | 7.33 | 9.24 | .8-1.4 mm |

P = porous particles
BG = solid bioactive glass control

The table above shows the various porous particles and control bioactive glass that was pre-reacted. These various iterations were used in further experiments with the collagen materials to form composites.

Experiment 4

The same collagen blend as in experiment 3 (2:1 ASG/DM3 at 10 mg/mL) was used along with porous particles that were pre-reacted at either 1 hr or 18 hours. The processing was the same for all samples. The 1 Hr pre-reacted samples behaved in the same manner as the unreacted particles; that is they did not absorb fluid readily, the material was fairly dense and not as porous as collagen alone, and when finally wet it did not retain the particles. The samples produced with the 18Hr pre-reacted particles fared much better. There was little pH rise after mixing, the slurry was able to be mixed and poured into molds before the slurry gelled, and the particles were retained in the composite. In addition, when liquid was placed on the surface of these samples the material adsorbed the liquid quite rapidly. In addition, the handling properties of the composite that used the pre-reacted particles were superior to the other samples.

There are a few other examples of passivating the surface of bioactive glass particles or subjecting them to solutions that contain proteins in order to make a surface that contains a reacted hydroxyapatite layer with proteins intermingles. In U.S. Pat. No. 5,977,204 bioactive glass particles are used as a filler in a resorbable polymer matrix. The surface passivated bioactive glass is reacted for 3 days in order to form a complete hydroxyapatite layer. It was found that this surface reacted layer produced a composite that had enhanced mechanical properties. The invention describes the passivation of the bioactive glass as being made incapable of reacting with water. This technology would prevent the bioactive glass particles in the current invention from further enhancing the bone regeneration through the further release of ions to the surrounding tissue and would therefore not be applicable to the composite devices of the current invention.

In U.S. Pat. No. 6,224,913 (and U.S. Pat. No. 6,413,538 and U.S. Pat. No. 6,549,466) the bioactive glass particles are subjected to repeated immersions in a number of different solutions in order to incorporate proteins within the hydroxyapatite layer that forms as a result of reactions. The presence of proteins within the bioactive particle surface would likely have adverse reactions with the side chains of the organic collagen molecule and the result would likely be constructs that do not absorb fluid and could possibly cause inflammatory responses.

We discovered that there is a limited range of reactivity of bioactive glass particles that forms a very thin HCA layer that isn't completely covering the surface of the particles and still allows the further reaction of the particles to release the ions that enhance bone regeneration and still provide the osteostimulative response of the composite.

Experiment 5

ASG/DM3 collagen, at 20 mg/mL was mixed with 90% by weight of 0.85 mm-1.4 mm bioactive glass particles. Two sets of particles were used; one pre-reacted for 6 hours and one reacted for 18 hours. In both cases, the slurry pH did not rise significantly after mixing in the particles; the material was mixed for 2 minutes and cast into molds. It was then placed in the lyophilizer and the samples were freeze-dried. Upon removal the materials were homogeneous, porous and of a uniform consistency. The samples all absorbed moisture rapidly, and when handled after the absorption of the liquid, they all maintained their structural integrity.

In addition to the above mentioned examples, it is possible, after the lyophilization process, to cross-link the composite, either with gluteraldehyde, or other chemical or enzymatic agents. The cross-linking will enhance the mechanical and structural integrity of the composites and will also improve the fluid adsorption.

Experiment 6

Two variations using 1:1 & 2:1 ASG/DM3 collagen ratios at 20 mg/ml were mixed with 90% by weight of 0.85 mm-1.4 mm bioactive glass particles. 18 hr pre-reacted particles were used and the slurry was poured into molds and cast. After the first lyophilization, the constructs were chemically crosslinked using glutaraldehyde in various concentrations. Three different concentrations of glutaraldehyde were used: 0.00125 (low), 0.0125 (med) & 0.125 (high) to evaluate the structural integrity and manipulation properties of the samples. The samples were tested for wicking ability as well as mechanical handling. The lowest and the medium concentration crosslinked samples remained homogenous and maintained uniform consistency.

Experiment 7

In this experiment, two levels in concentration of the chemical crosslinking agent glutaraldehyde between the lowest and the medium levels were evaluated for the next set of samples. $6.25 \times 10^{-3}$ & $9.4 \times 10^{-3}$ levels of glutaraldehyde were used keeping the particle size of 18 hr pre-reacted bioactive glass particles at 0.85 mm-1.4 mm and the collagen ratio (ASG/DM3) at 2:1. The samples were evaluated again for their handling properties and wickability with equal volume of liquids.

Experiment 8

The next experiments involved incorporation of smaller particle sizes into the pre-reacted bioactive glass mixture. The new samples that were generated used 0.5 mm-1.4 mm particles. Collagen ratio was constant as previous experiment ASG/DM3@2:1 and the slurry was poured into molds and lyophilized. Upon removal from the first lyophilization cycle, the samples were treated with two levels of crosslinking: $6.25 \times 10^{-3}$ & $9.4 \times 10^{-3}$. The samples again were evaluated for homogeneity and structural integrity after absorption of an equal volume of liquid.

Experiment 9

The next set of experiments evaluated the effect of lyophilization on varying sizes of the samples. Two sizes of samples: 25 mm×50 mm×4 mm & 25 mm×50 mm×8 mm were generated using 90% by weight of 0.5 mm-1.4 mm pre-reacted bioactive glass morsels mixed with 2:1 ASG/DM3 collagen@20 mg/ml and chemically crosslinked at 6.25×10(−3) using glutaraldehyde. The samples obtained were evaluated again for homogeneity, shrinkage and structural integrity after wetting.

The invention claimed is:

1. A bone regenerative composition including 2-20% collagen and 80-98% bioactive glass, wherein the composition is free from calcium phosphate.

2. The bone regenerative composition of claim 1, wherein the bioactive glass has a porosity of up to 90%.

3. The bone regenerative composition of claim 1, wherein the bioactive glass has pores ranging from about 10 to about 5100 microns.

4. The bone regenerative composition of claim 1, wherein the bioactive glass has average pore size of 100 microns plus or minus 50 microns.

5. The bone regenerative composition of claim 1, wherein the bioactive glass has average pore size of 200 microns plus or minus 50 microns.

6. The bone regenerative composition of claim 1, wherein the bioactive glass has average pore size of 300 microns plus or minus 50 microns.

7. The bone regenerative composition of claim 1, wherein the bioactive glass has average pore size of 400 microns plus or minus 50 microns.

8. The bone regenerative composition of claim 1, wherein the bioactive glass has average pore size of 500 microns plus or minus 50 microns.

9. The bone regenerative composition of claim 1, wherein the bioactive glass has average pore size of 600 microns plus or minus 50 microns.

10. The bone regenerative composition of claim 1, wherein the bioactive glass has average pore size of 700 microns plus or minus 50 microns.

11. The bone regenerative composition of claim 1, including 3-10% collagen and 90-97% bioactive glass.

12. The bone regenerative composition of claim 1, further comprising an extracellular matrix molecule selected from the group consisting of integrins, fibronectin, vitronectin, osteopontin, bone sialoprotein thrombospondin, and fibrinogen, or a homo or copolymer of glycolides, acrylates, lactic acids, and caprolactone.

13. The bone regenerative composition of claim 1, wherein said composition is crosslinked.

14. The bone regenerative composition of claim 1, wherein said composition is freeze-dried.

15. The bone regenerative composition of claim 1, including 3% collagen and 97% bioactive glass.

16. The bone regenerative composition of claim 15, wherein said composition is crosslinked.

17. The bone regenerative composition of claim 15, wherein said composition is freeze-dried.

* * * * *